(12) United States Patent
Lee et al.

(10) Patent No.: US 8,244,487 B2
(45) Date of Patent: Aug. 14, 2012

(54) MEASURING SYSTEM

(75) Inventors: Wei-Chen Lee, Taipei (TW);
Ming-Chung Wu, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 378 days.

(21) Appl. No.: 12/534,747

(22) Filed: Aug. 3, 2009

(65) Prior Publication Data

US 2010/0305878 A1    Dec. 2, 2010

(30) Foreign Application Priority Data

Jun. 2, 2009 (TW) ............................... 98118145 A

(51) Int. Cl.
*G01L 5/00* (2006.01)
*G06F 15/00* (2006.01)
(52) U.S. Cl. ........... 702/43; 702/127; 702/158; 702/159
(58) Field of Classification Search ............... 702/43–45, 702/158–159, 188–189, 127
See application file for complete search history.

(56) References Cited

U.S. PATENT DOCUMENTS 5,020,904 A * 6/1991 McMahan, Jr. ............... 356/35.5
2004/0057054 A1 * 3/2004 Toyooka et al. ............... 356/496

* cited by examiner

*Primary Examiner* — Phuong Huynh

(57) ABSTRACT

A measuring system for tensile or compressive tests is provided. A set of mirrors includes a first plane mirror and a second plane mirror. The angles between the first plane mirror and the first axis and between the second plane mirror and the first axis are both a specific included angle, such that the first and second plane mirrors are symmetrical to the first axis. An object to be tested is disposed between the set of mirrors and an image capturing apparatus. Two extremities of the object have the first and second labels, respectively. The first and second mirror images of the first and second labels are generated through the first and second plane mirrors, respectively. After the object is tensed or compressed, the image capturing apparatus obtains the displacement of the first and second labels according to the shifting of the first and second mirror images.

12 Claims, 5 Drawing Sheets

MEASURING SYSTEM

CROSS REFERENCE TO RELATED APPLICATIONS

This Application claims priority of Taiwan Patent Application No. 098118145, filed on Jun. 2, 2009, the entirety of which is incorporated by reference herein.

BACKGROUND OF THE INVENTION

1. Field of the Invention

The invention relates to a measuring system, and more particularly to a measuring system for a tensile or compressive test.

2. Description of the Related Art

In general, tensile or compressive tests are used to test the resistance capability for a material that sustains loading (tension) in a quiescent state or increasing state. In a tensile test, two extremities of a test sheet are clamped and the tension along the axial directions are applied to the two extremities of the test sheet, such that the test sheet is lengthened along a direction parallel with the acting force. In a compressive test, two extremities of a test sheet are clamped and pressure along the axial directions are applied to the two extremities of the test sheet, such that the test sheet is shortened along a direction parallel with the acting force.

FIG. 1A shows a conventional measuring system which uses a single camera to measure the displacements of two extremities of an object to be tested. As shown in FIG. 1A, a camera 110 is coupled to a personal computer (PC) 130 and simultaneously captures the variations of the labels A and B of an object 120. In the measuring system, the camera 110 must be disposed apart from the object 120, so as to capture the label A and the label B at the same time. Therefore, each pixel of the camera 110 may represent a longer distance than actual, such that the image resolution obtained by the PC 130 is inaccurate, thus causing measurement errors. FIG. 1B shows another conventional measuring system which uses two cameras to measure the displacement of two extremities of an object to be tested, respectively. In the measuring system, the two cameras 110 and 110B are used to measure the variations of the labels A and B of an object 120, respectively. Thus, a higher image resolution is obtained due to each camera capturing only one label. However, using two cameras increase costs.

BRIEF SUMMARY OF THE INVENTION

A measuring system for tensile or compressive tests is provided. An exemplary embodiment of such a measuring system for tensile or compressive tests comprises: an image capturing apparatus capturing images along a first axis, a set of mirrors comprising a first plane mirror and a second plane mirror, and an object to be tested, disposed between the set of mirrors and the image capturing apparatus and orthogonal to the first axis. An angle between the first plane mirror and the first axis and an angle between the second plane mirror and the first axis are both a specific included angle, such that the first and second plane mirrors are symmetrical to the first axis. Two extremities of the object have a first label and a second label, respectively. A first mirror image of the first label and a second mirror image of the second label are generated through the first and second plane mirrors, respectively. After the object is tensed or compressed, the image capturing apparatus obtains the displacement quantities of the first and second labels according to the shifting of the first mirror image and the second mirror image.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
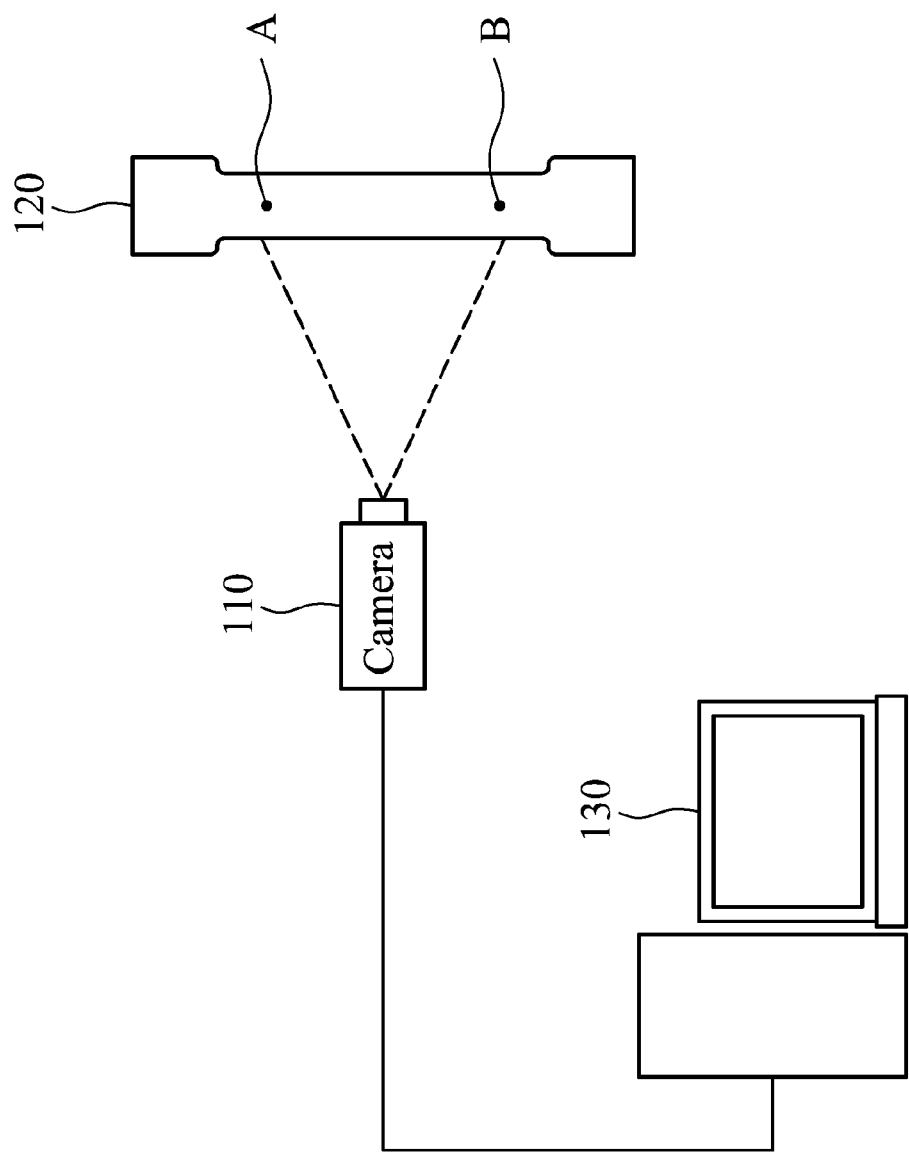
FIG. 1A shows a conventional measuring system which uses a single camera to measure the displacements of two extremities of an object to be tested.
Figure 1B:
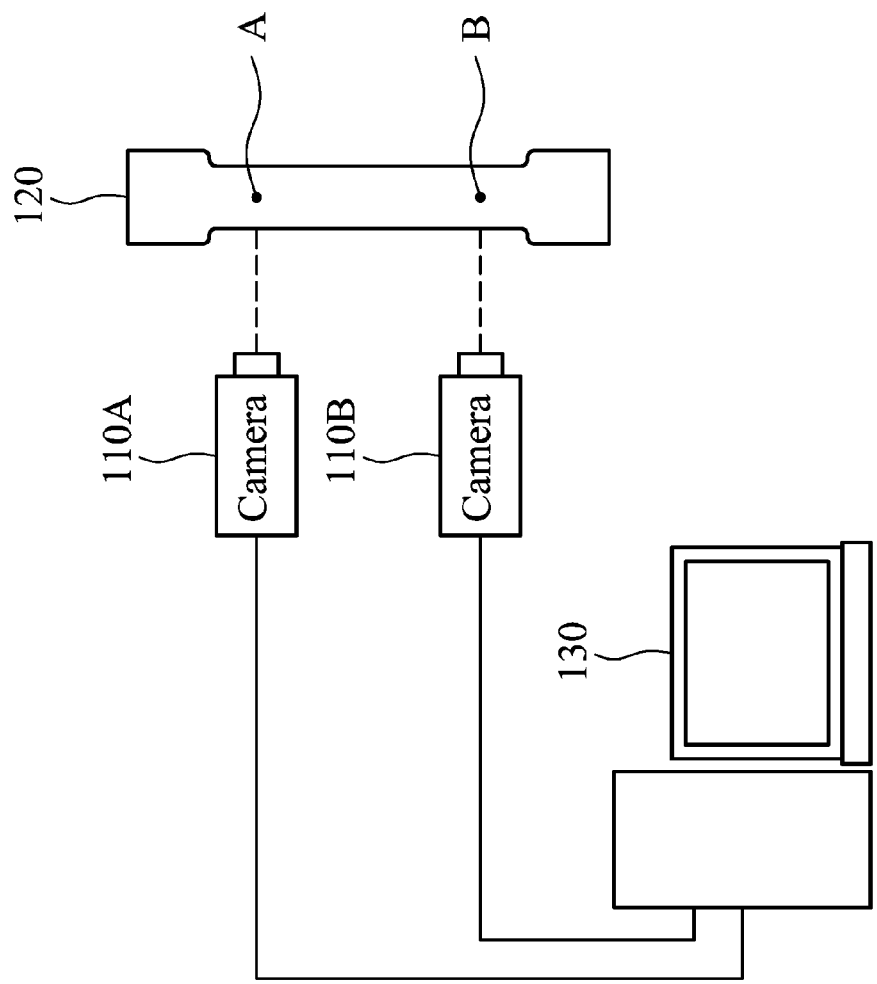
FIG. 1B shows another conventional measuring system which uses two cameras to measure the displacements of two extremities of an object to be tested, respectively.
Figure 2:
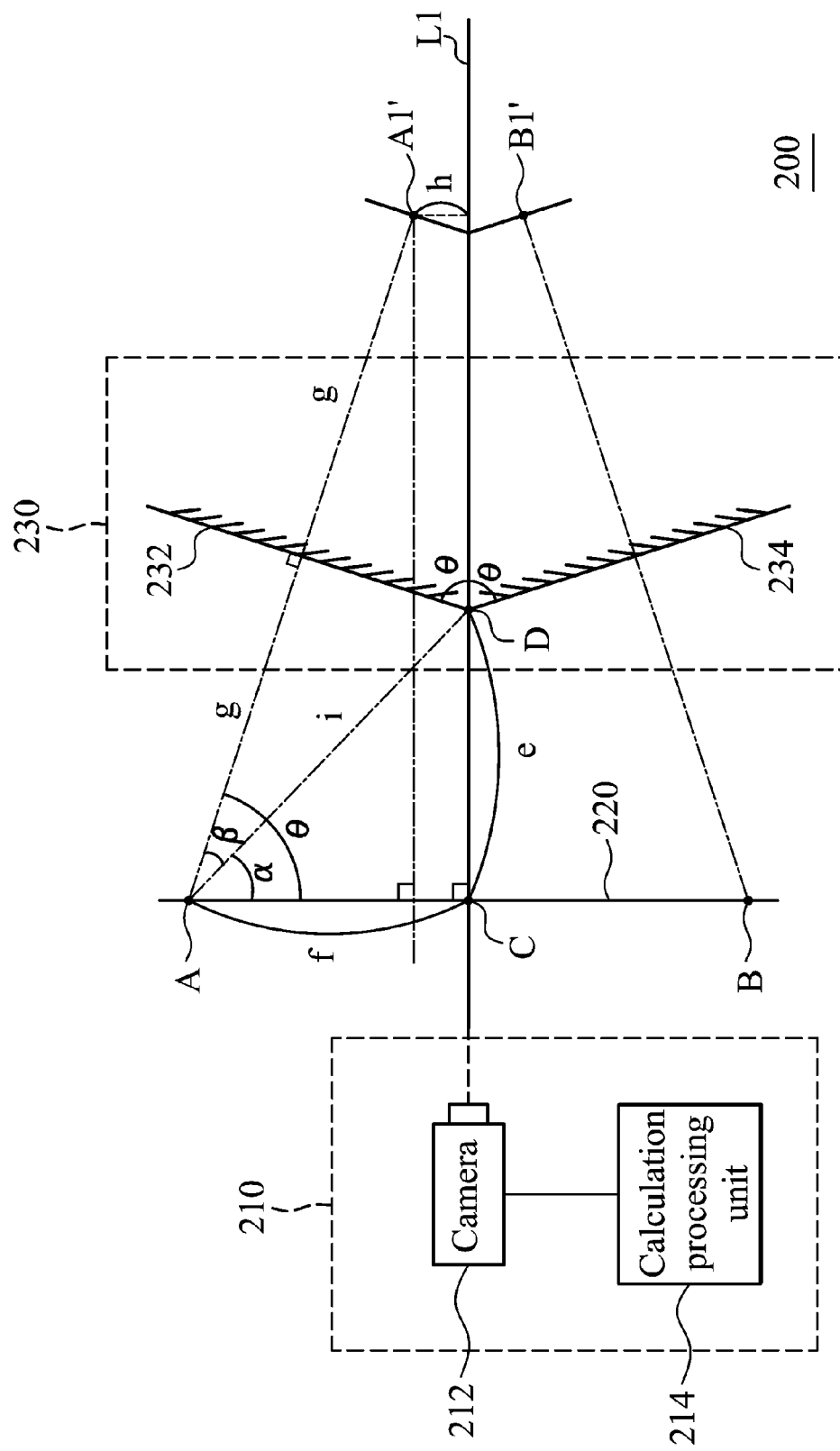
FIG. 2 shows a schematic illustrating a measuring system according to an embodiment of the invention.
Figure 3:
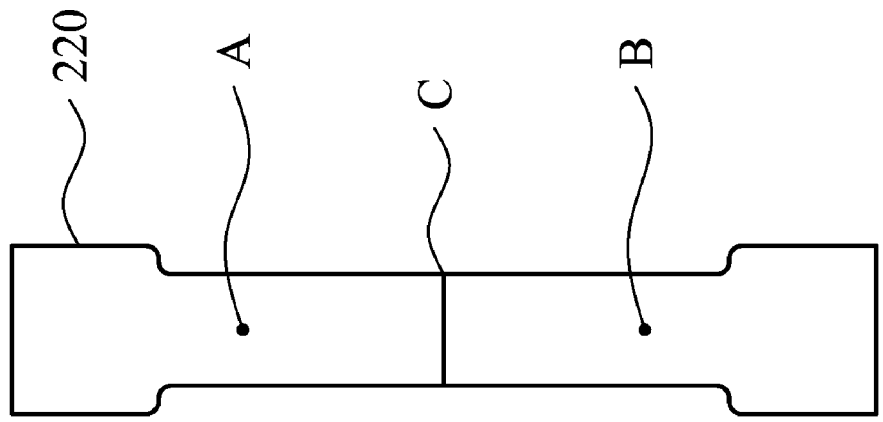
FIG. 3 shows a schematic illustrating an object to be tested according to an embodiment of the invention.

FIG. 2 shows a schematic illustrating a measuring system 200 according to an embodiment of the invention, wherein the measuring system 200 is used to perform tensile or compressive tests for various materials. The measuring system 200 comprises an image capturing apparatus 210, an object 220 to be tested and a set of mirrors 230 formed by a first plane mirror 232 and a second plane mirror 234. The image capturing apparatus comprises a camera 212 for capturing images along a first axis L1 which faces a lens center of the camera 212. In the embodiment, the first plane mirror 232 is connected with the second plane mirror 234, which forms an intersection D in the first axis L1. In one embodiment, the first plane mirror 232 is disconnected with the second plane mirror 234, wherein the extensions of the first plane mirror 232 and the second plane mirror 234 may intersect at the intersection D of the first axis L1. Furthermore, an angle between the first plane mirror 232 and the first axis L1 and an angle between the second plane mirror 234 and the first axis L1 are both the included angle θ, such that the first plane mirror 232 and the second plane mirror 234 are symmetrical to the first axis L1, wherein the included angle θ is an acute angle. In the embodiment, the object 220 may be a test sheet for any materials to be tested. The object 220 is disposed between the image capturing apparatus 210 and the set of mirrors 230, and the object 220 is orthogonal to the first axis L1, wherein a center C of the object 220 is disposed in the first axis L1 and two extremities of the object 220 have a label A and a label B, respectively, as shown in FIG. 3.

Referring to FIG. 2, the labels A and B of the object 220 are symmetrical to the first axis L1, thus a distance between the label A and the first axis L1 and a distance between the label B and the first axis L1 are both the length f. Moreover, in the first axis L1, a distance between the center C of the object 220 and the intersection D is a length e. According to imaging principle, a mirror image A1' of the label A is generated through the first plane mirror 232, wherein a distance between the label A and the first plane mirror 232 and a distance between the mirror image A1' and the first plane mirror 232 are both the length g for a direction that is orthogonal to the first plane mirror 232. Furthermore, a distance between the mirror image A1' and the first axis L1 is a length h. Similarly, a mirror image B1' of the label B is generated through the second plane mirror 234. As known in the art, the mirror image A1' and the mirror image B1' are the virtual images formed by reflection in the first plane mirror 232 and the second plane mirror 234, respectively.

First, a cosine value cos θ of a right triangle formed by the label A, the mirror image A1' and the object 220 may be given by the following equation (1):

$$\cos\theta = \frac{f-h}{2g}. \quad (1)$$

In addition, an angle α and a hypotenuse length i of a right triangle formed by the label A, the center C of the object 220 and the intersection D may be given by the following equations (2) and (3), respectively:

$$\alpha = \tan^{-1}\frac{e}{f}; \quad (2)$$

and $$i = \sqrt{f^2 + e^2}. \quad (3)$$

Next, a cosine value cos β of a right triangle formed by the label A, the intersection D and the first plane mirror 232 may be given by the following equation (4):

$$\cos\beta = \cos(\theta - \alpha) = \frac{g}{i}. \quad (4)$$

Next, by using the equations (1)-(4), an actual value of the length h (the distance between the mirror image A1' and the first axis L1) may be obtained, as shown in the following equation (5):

$$\begin{aligned} h &= f - 2g \times \cos\theta \\ &= f - 2[\cos(\theta - \alpha) \times i] \times \cos\theta \\ &= f - 2\left[\cos(\theta - \alpha) \times \sqrt{f^2 + e^2}\right] \times \cos\theta \\ &= f - 2\left[\cos\left(\theta - \tan^{-1}\frac{e}{f}\right) \times \sqrt{f^2 + e^2}\right] \times \cos\theta, \end{aligned} \quad (5)$$

wherein the length e, the length f and the angle θ are known. Furthermore, the image capturing apparatus 210 further comprises a calculation processing unit 214 for obtaining the actual value of the length h according to the length e, the length f and the angle θ. In one embodiment, the calculation processing unit 214 may be a personal computer (PC). A distance between the mirror image B1' and the first axis L1 is also the length h as the labels A and B are symmetrical to the first axis L1 and the first and second plane mirrors 232 and 234 are also symmetrical to the first axis L1.

Figure 4:
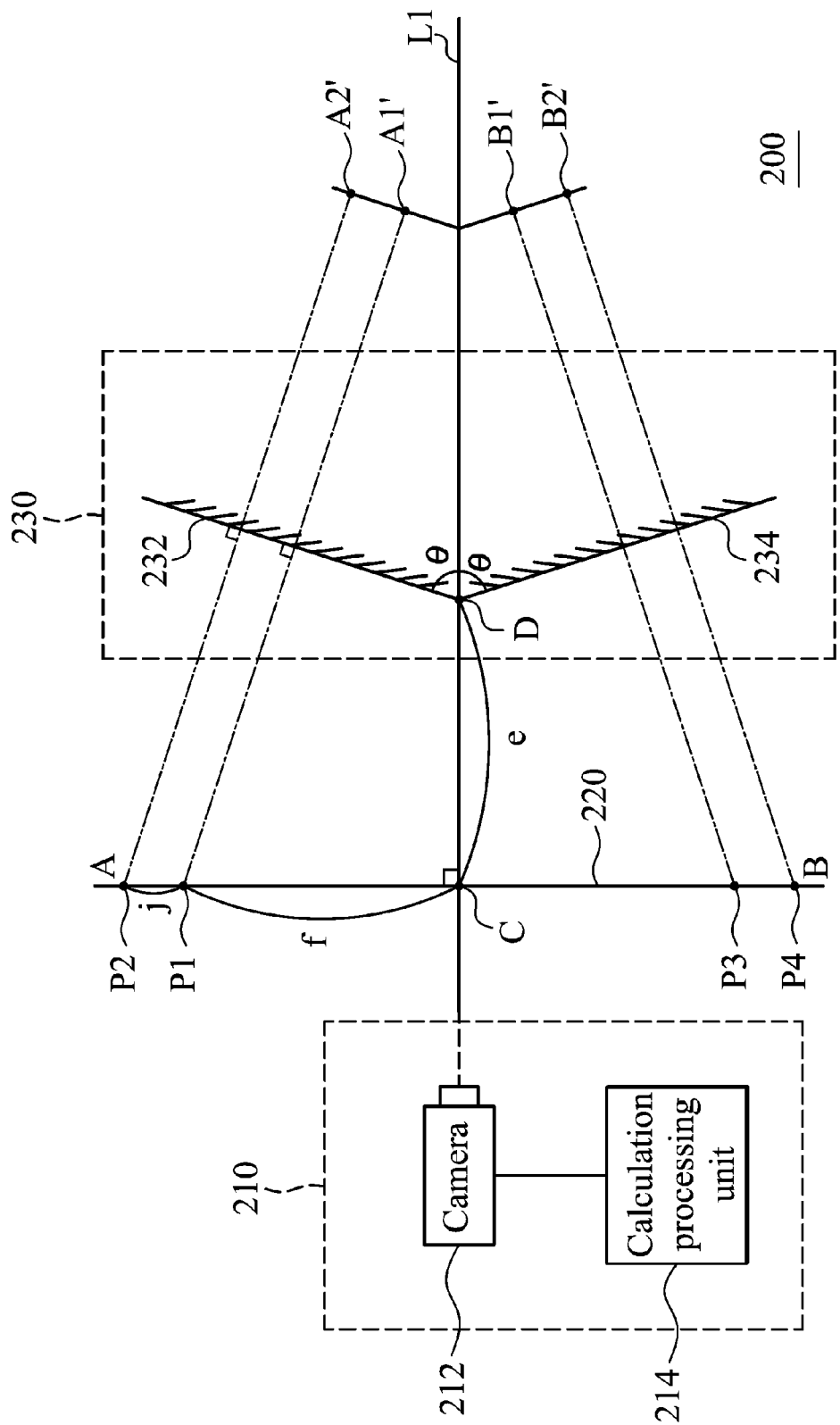
FIG. 4 shows a schematic illustrating that the object of FIG. 2 has been tensed.

FIG. 4 shows a schematic illustrating that the object 220 of FIG. 2 has been tensed. By applying the tensions (not shown) to the two extremities of the object 220, the distance from the label A to the first axis L1 and the distance from the label B to the first axis L1 may lengthen. As shown in FIG. 4, a location of the label A has been changed from a point P1 to a point P2, and a mirror image A2' of the label A is generated through the first plane mirror 232. Similarly, a location of the label B has been changed from a point P3 to a point P4, and a mirror image B2' of the label B is generated through the second plane mirror 234. In the image capturing apparatus 210, the camera 212 may capture the mirror image A2', and the calculation processing unit 214 may obtain a displacement quantity j from the point P1 to the point P2 according to a distance between the mirror image A2' and the first axis L1, i.e. the label A shifts by the length j. Similarly, the calculation processing unit 214 may also obtain a length that the label B has shifted according to a displacement quantity between the mirror image B1' and the mirror image B2'. Therefore, the calculation processing unit 214 may obtain a strain of the object 220 according to the tensed lengths of the labels A and B and the applied tensions.

In tensile or compressive tests, by disposing two plane mirrors in a specific angle according to the invention, a single camera may simultaneously capture each mirror image of the labels of a test sheet to be tested through the corresponding plane mirrors during a nearer range, such that the calculation processing unit may obtain accurate measure values according to a higher image resolution. Furthermore, when the test sheet is tensed or compressed, a distance between two labels of the test sheet and a relative position variation rate of the two labels are obtained by image processing and calculation by the image capturing apparatus.

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. A measuring system for tensile or compressive test, comprising:
   an image capturing apparatus capturing images along an axis;
   a set of mirrors comprising a first plane mirror extending in a first direction and a second plane mirror extending in a second direction, wherein the extensions of the first and second plane mirrors intersect at a specific point of the axis, wherein an angle between the extension of the first plane mirror and the axis and an angle between the extension of the second plane mirror and the axis are both a specific included angle, such that the first and second plane mirrors are symmetrical to the axis; and
   an object to be tested, disposed between the set of mirrors and the image capturing apparatus and orthogonal to the axis, wherein two extremities of the object have a first label and a second label, respectively, and a first mirror image of the first label and a second mirror image of the second label are generated through the first and second plane mirrors, respectively,
   wherein after the object is tensed or compressed, the image capturing apparatus obtains the displacement quantities of the first and second labels according to a third mirror image of the first label of the tensed or compressed object, a fourth mirror image of the second label of the tensed or compressed object, the first mirror image and the second mirror image.

2. The measuring system as claimed in claim 1, wherein the first label and the second label are symmetrical to the axis, and a distance between the first label and the axis and a distance between the second label and the axis are both a first length.

3. The measuring system as claimed in claim 2, wherein a distance between the object and the specific point is a second length for the axis.

4. The measuring system as claimed in claim 3, wherein the third mirror image of the first label of the tensed or compressed object is generated through the first plane mirror, and a distance between the first mirror image and the axis is a third length and a distance between the third mirror image and the axis is a fourth length.

5. The measuring system as claimed in claim 4, wherein the image capturing apparatus obtains the displacement quantity of the first label of the tensed or compressed object according to the third and fourth lengths.

6. The measuring system as claimed in claim 3, wherein a distance between the first mirror image and the axis is $$f - 2\left[\cos\left(\theta - \tan^{-1}\frac{e}{f}\right) \times \sqrt{f^2 + e^2}\right] \times \cos\theta,$$

wherein θ represents the specific included angle, f represents the first length and e represents the second length.

7. The measuring system as claimed in claim 1, wherein the image capturing apparatus comprises a camera and a calculation processing unit, wherein the camera captures the images of the first and second labels through the first and second plane mirrors simultaneously, and the calculation processing unit obtains the displacement quantities of the first and second labels of the tensed or compressed object according to the mirror images generated through the first and second plane mirrors.

8. The measuring system as claimed in claim 7, wherein a lens center of the camera faces the axis.

9. The measuring system as claimed in claim 1, wherein the specific included angle is an acute angle.

10. The measuring system as claimed in claim 1, wherein the image capturing apparatus obtains a strain of the object according to the displacement quantities of the first and second labels.

11. The measuring system as claimed in claim 3, wherein the fourth mirror image of the second label of the tensed or compressed object is generated through the second plane mirror, and a distance between the second mirror image and the axis is a third length and a distance between the fourth mirror image and the axis is a fourth length.

12. The measuring system as claimed in claim 11, wherein the image capturing apparatus obtains the displacement quantity of the second label of the tensed or compressed object according to the third and fourth lengths.

\* \* \* \* \*